United States Patent
Chand et al.

(10) Patent No.: US 6,762,316 B1
(45) Date of Patent: Jul. 13, 2004

(54) PREPARATION OF SUBSTITUTED CYCLOPENTANE AND CYCLOPENTENE COMPOUNDS AND CERTAIN INTERMEDIATES

(75) Inventors: Pooran Chand, Birmingham, AL (US); Arthur J. Elliott, Apex, NC (US)

(73) Assignee: BioCryst Pharmaceuticals, Inc., Birmingham, AL (US)

( * ) Notice: Subject to any disclaimer, the term of this patent is extended or adjusted under 35 U.S.C. 154(b) by 0 days.

(21) Appl. No.: 10/019,217

(22) PCT Filed: Jun. 28, 2000

(86) PCT No.: PCT/US00/17685
§ 371 (c)(1),
(2), (4) Date: May 13, 2002

(87) PCT Pub. No.: WO01/00558
PCT Pub. Date: Jan. 4, 2001

Related U.S. Application Data

(60) Provisional application No. 60/140,840, filed on Jun. 28, 1999.

(51) Int. Cl.$^7$ .......................... C07C 69/74; C07C 13/11; C07C 13/12
(52) U.S. Cl. ....................................... 560/126; 564/146
(58) Field of Search ........................... 560/126; 564/146

(56) References Cited

FOREIGN PATENT DOCUMENTS

WO    99/33781   *   7/1999

OTHER PUBLICATIONS

Park et al., "Diastereoselective Synthesis of Cyclopentanoids with Hydantoin and Isoxazoline Substituents", J.Org. Chem, 1998, vol. 63, No. 1, pp. 113–117.

* cited by examiner

Primary Examiner—Taofiq Solola
(74) Attorney, Agent, or Firm—Connolly Bove Lodge & Hutz LLP

(57) ABSTRACT

The invention relates to methods for preparing substituted cyclopentene compounds, their intermediates and use as neuraminidase inhibitors.

1 Claim, No Drawings

PREPARATION OF SUBSTITUTED CYCLOPENTANE AND CYCLOPENTENE COMPOUNDS AND CERTAIN INTERMEDIATES

This appln is a 371 of PCT/US00/17685 filed Jun. 28, 2000 and claims the benefit of appln No. 60/140,840 filed Jun. 28, 1999.

TECHNICAL FIELD

This invention relates to methods for preparing certain substituted cyclopentane compounds and certain intermediates thereof. The present invention is also concerned with novel intermediates or precursors for producing the substituted cyclopentane compounds. Substituted cyclopentane compounds prepared according to the present invention are useful as neuraminidase inhibitors, and especially in pharmaceutical composition for preventing, treating or ameliorating viral, bacterial and other infections.

BACKGROUND OF THE INVENTION

Despite the wealth of information available, influenza remains a potentially devastating disease of man, lower mammals, and birds. No effective vaccine exists and no cure is available once the infection has been initiated.

Influenza viruses consist of eight pieces of single stranded RNA, packaged in orderly fashion within the virion. Each piece codes for one of the major viral proteins. The replication complex is enclosed with a membrane composed of matrix protein associated with a lipid bilayer. Embedded in the lipid bilayer are two surface glycoprotein spikes, hemagglutinin (HA) and the enzyme neuraminidase (NA). All of the viral genes have been cloned and the three-dimensional structures of the surface glycoproteins have been determined.

Influenza viruses continually undergo antigenic variation in the two surface antigens, HA and NA, toward which neutralizing antibodies are directed. For this reason, vaccines and a subject's natural immune system have not been very effective. Attention is now being directed to finding other potential antiviral agents acting at other sites of the virion.

Furthermore, many other organisms carry NA. Many of these NA-possessing organisms are also major pathogens of man and/or mammals, including *Vibraeo cholerae, Clostridium perfringes, Streptococcus pneumonia, Arthrobacter sialophilas,* and other viruses, such as parainfluenza virus, mumps virus, Newcastle disease virus, fowl plague virus, and Sendai virus. Compounds of this invention are also directed to inhibiting NA of these organisms.

In viruses, NA exists as a tetramer made of four roughly spherical subunits and a centrally-attached stalk containing a hydrophobic region by which it is embedded in the organism's membrane. Several roles have been suggested for NA. The enzyme catalyzes cleavage of the α-ketosidic linkage between terminal sialic acid and an adjacent sugar residue. Removal of the sialic acid lowers the viscosity and permits access of the virus to the epithelial cells. NA also destroys the HA receptor on the host cell, thus allowing elution of progeny virus particles from infected cells.

Research indicates that the active site for influenza neuraminidase remains substantially unchanged for the major strains of influenza. For example, a comparison of sequences from influenza A subtypes and influenza B shows conserved residues with crucial structural and functional roles. Even though the sequence homology is only about 30%, many of the catalytic residues are conserved. Furthermore, the three-dimensional structures of influenza A and B neuraminidases have been determined. Superposition of the various structures shows remarkable structural similarity of the active site. Since the active site amino acid residues are conserved in all known influenza A neuraminidases that have been sequenced so far, an inhibitor that is effective against different strains of influenza A and/or B neuraminidase can be designed based on the three-dimensional structure of a neuraminidase.

In general, the role of NA is thought to be for the mobility of the virus both to and from the site of infections. Compounds that inhibit neuraminidase's activity may protect a subject from infection and/or cure a subject once infection has set in.

Analogs of neuraminic acid, such as 2-deoxy-2,3-didehydro-N-acetylneuraminic acid (DANA) and its derivatives are known to inhibit HA in vitro; however, these compounds are inactive in vivo. Palese and Schulman, in CHEMOPROPHYLAXIS AND VIRUS INFECTION OF THE UPPER RESPIRATORY TRACT, Vol. 1 (J. S. Oxford, Ed.), CRC Press, 1977, at PS 189–205.

Von Itzstein et al. describes cyclohexane analogs of α-D-neuraminic acid of the formula

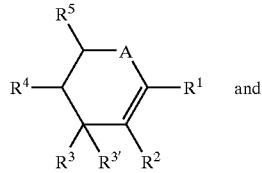

and

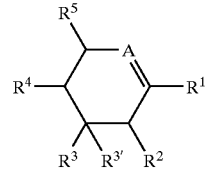

wherein:
A is O, C or S in Formula (a), and N or C in Formula (b);
$R^1$ is $CO_2H$, $PO_3H_2$, $NO_2$, $SO_2H$, $SO_3H$, tetrazolyl-, $CH_2CHO$, CHO, or $CH(CHO)_2$;
$R^2$ is H, $OR^6$, F, Cl, Br, CN, $NHR^6$, $SR^6$ or $CH_2X$, where X is $NHR^6$ halogen, or $OR^6$;
$R^3$ and $R^{3'}$ are H, CN, $NHR^6$, $SR^6$, $=NOR^6$, $OR^6$, guanidino, $NR^6$;
$R^4$ is $NHR^6$, $SR^6$, $OR^6$, $CO_2R^6$, $NO_2$, $C(R^6)_3$, $CH_2CO_2R^6$, $CH_2NO_2$ or $CH_2NHR^6$;
$R^5$ is $CH_2YR^6$, $CHYR^6CH_2YR^6$ or $CHYR^6CHYR^6CH_2YR^6$;
$R^6$ is H, acyl, alkyl, allyl, or aryl;
Y is O, S, NH, or H;
and pharmaceutical salts thereof, useful as antiviral agents.

In addition, certain benzene derivatives are suggested in U.S. Pat. No. 5,453,533 as being inhibitors of influenza virus neuraminidase and various others are disclosed in U.S. patent application Ser. No. 08/413,886. Yamamoto et al. describe various sialic acid isomers as having inhibitory activity against neuraminidase in *Synthesis of Sialic Acid Isomers With Inhibitory Activity Against Neuraminidase,* TETRAHEDRON LETTERS, Vol. 33, No. 39, pp. 5791–5794, 1992.

WO 96/26933 to Gilead Sciences, Inc. describes certain 6-membered ring compounds as possible inhibitors of neuraminidase.

More recently, there have been disclosed new cyclopentane derivatives that are useful as neuraminidase inhibitors. For example, see WO 96/30329, assigned to BioCryst Pharmaceuticals, Inc., the assignee of the present application, the entire disclosure of which being incorporated herein by reference.

SUMMARY OF INVENTION

The present invention relates to methods for preparing certain substituted cyclopentane compounds that are useful as inhibitors of the enzyme neuraminidase. Moreover, the present invention is concerned with a method for preparing certain precursors of the substituted cyclopentane compounds.

The substituted cyclopentane compounds prepared according to the present invention are represented by the following formulae 1a and 1b:

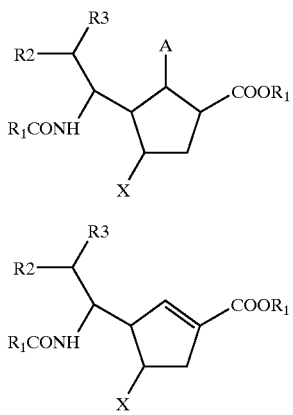

wherein each $R_1$ individually is alkyl or substituted alkyl, alkenyl or substituted alkenyl of 1–6 carbon atoms, or H; each of $R_2$ and $R_3$ individually is alkyl or alkenyl of 1–8 carbon atoms, cycloalkyl or substituted cycloalkyl of 4–8 carbon atoms, aryl or substituted aryl, arylalkyl or substituted arylalkyl, or H provided at least one of $R_2$ and $R_3$ is other than H; X is $NHR_1$, NHC (=NH) $NHR_4$ where $R_4$ is H, alkyl of 1–6 carbon atoms, $OR_1$, $COR_1$, $COOR_1$, CN or $NO_2$; A is H, F, $OR_1$, $OCOR_1$, —$OOCNHR_1$, $NHR_1$, or $NHCOOR_1$; and
pharmaceutically acceptable salts thereof.

The precursors according to the present invention are isoxazoline derivatives represented by the following formula 4:

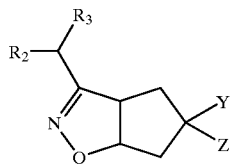

wherein $R_2$ and $R_3$ are the same as defined above and wherein each of Y and Z individually is $COOR_1$ or H provided that at least one of Y and Z is other than H.

The isoxazoline derivatives according to formula 4 are prepared according to the following procedure:

A nitrile oxide of the formula 2

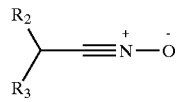

is reacted with a cyclopentene derivative of the formula 3 to produce the desired isoxazoline derivative. $R_2$, $R_3$, Y and Z are the same as defined above.

The cyclopentane compounds of formula 1a can be prepared from the above isoxazoline derivatives by reducing the isoxazoline derivatives of formula 4 to form an aminoalcohol derivative according to formula 5. Reacting the aminoalcohol compound of formula 5 with an anhydride or acid halide of a carboxylic acid of the formula: $R_1COOH$ to produce the acylated compounds represented by formula 6. Next, the alcohol group of the acylated compounds is converted into a leaving group which in turn is displaced by ammonia or guanidine to produce compounds of formula 1a or the leaving group is displaced by an azide ion which in turn is converted to the guanidine using $NH_2$ compound.

In an alternative process for preparing the cyclopentane compounds of formula 1a, an isoxazoline compound of formula 4 is converted to ketone according to formula 7

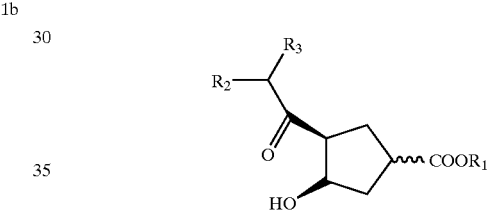

by opening its isoxazoline ring. The ketone of formula 7 is subjected to reductive amination to form a compound according to formula 8

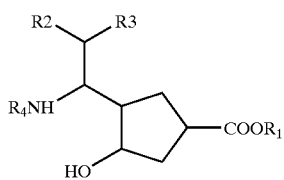

wherein $R_4$ is H or a substituted benzyl. When $R_4$ is a substituted benzyl, such is removed to give the aminoalcohol compounds of formula 5. The aminoalcohols are then converted to the final product as discussed above.

According to a still further aspect of the present invention, cyclopentane derivatives of formula 9 can be reacted with a nitrile oxide of formula 2 to give the isoxazoline derivatives 10 as shown in Scheme 2. Such isoxazolines may be converted to compounds 12 and may further be dehydrated to give the unsaturated compounds 13. Alternatively, the OH may be converted to $NH_2$ or F by conventional methods known in the art to afford compounds 14 and 15 respectively.

It is a further object of this invention to provide a method of using compounds of this invention for treating and/or curing a viral infection.

BEST AND VARIOUS MODES FOR CARRYING OUT INVENTION

The substituted cyclopentane compounds prepared according to the present invention are represented by the following formulae 1a and 1b:

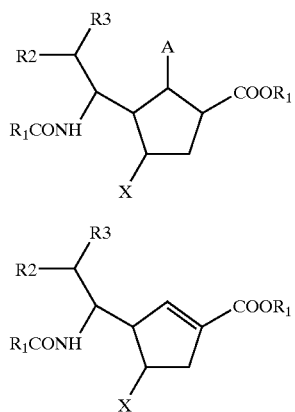

wherein each $R_1$ individually is alkyl or substituted alkyl of 1–6 carbon atoms, alkenyl or substituted alkenyl of 1–6 carbon atoms, or H; each of $R_2$ and $R_3$ individually is alkyl or alkenyl of 1–8 carbon atoms, cycloalkyl or substituted cycloalkyl of 4–8 carbon atoms, aryl or substituted aryl, arylalkyl or substituted arylalkyl, or H provided at least one of $R_2$ and $R_3$ is other than H; X is $NHR_1$, $NHC(=NH)NHR_4$ where $R_4$ is H, alkyl of 1–6 carbon atoms, $OR_1$, $COR_1$, $COOR_1$ CN or $NO_2$; A is H, F, $OR_1$, $OCOR_1$, $—OOCNHR_1$, $NHR_1$, or $NHCOOR_1$; and pharmaceutically acceptable salts thereof.

The alkyl groups contain 1 to about 8 carbon, and preferably 1 to about 3 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. Examples of suitable cyclic aliphatic groups typically contain 4–8 carbon atoms and include cyclopentyl and cyclohexyl. The aromatic or aryl groups are preferably phenyl or alkyl substituted aromatic groups (aralkyl) such as phenyl $C_{1-3}$ alkyl such as benzyl.

Examples of substituted cycloalkyl groups include cyclic aliphatic groups typically containing 4–8 carbon atoms in the ring substituted with alkyl groups typically having 1–6 carbon atoms and/or hydroxy group. Usually 1 or 2 substituted groups are present.

The lower alkylene group can be straight, branched chain or cyclic unsaturated hydrocarbon group and contains 2–8 carbon atoms and preferably 2–3 carbon atoms. Examples of alkylene groups are vinyl, 1-propenyl, allyl, isopropenyl, 2-methyl-2-propenyl and cyclopentenyl.

Pharmaceutically acceptable salts of the compounds of formula (I) include those derived from pharmaceutically acceptable, inorganic and organic acids and bases. Examples of suitable acids include hydrochloric, hydrobromic, sulphuric, nitric, perchloric, fumaric, maleic, phosphoric, glycollic, lactic, salicyclic, succinic, p-toluenesulphonic, tartaric, acetic, citric, methanesulphonic, formic, benzoic, malonic, naphthalene-2-sulphonic, trifluoroacetic and benzenesulphonic acids.

Salts derived from appropriate bases include alkali such as sodium and ammonia.

Examples of some specific compounds within the scope of the present invention are:

t-3-(1-Acetylamino-2-ethyl)butyl-c-4-(aminoimino)methylamino-t-2-hydroxycyclopentane-r-1-carboxylic acid;

t-3-(1-Acetylamino-2-ethyl)butyl-c-4-amino-t-2-hydroxycyclopentane-r-1-carboxylic acid;

t-3-(1-Acetylamino-2-ethyl)butyl-c-4-(aminoimino)methylaminocyclopentane-r-1-carboxylic acid;

t-3-(1-Acetylamino-2-ethyl)butyl-c-4-aminocyclopentane-r-1-carboxylic acid;

Ethyl t-3-(1-Acetylamino-2-ethyl)butyl-c-4-(aminoimino)methylamino-t-2-hydroxycyclopentane-r-1-carboxylate;

Ethyl t-3-(1-Acetylamino-2-ethyl)butyl-c-4-amino-t-2-hydroxycyclopentane-r-1-carboxylate;

Ethyl t-3-(1-Acetylamino-2-ethyl)butyl-c-4-(aminoimino)methylaminocyclopentane-r-1-carboxylate;

Ethyl t-3-(1-Acetylamino-2-ethyl)butyl-c-4-aminocyclopentane-r-1-carboxylate;

t-3-(1-Acetylamino-2-propyl)pentyl-c-4-(aminoimino)methylamino-t-2-hydroxycyclopentane-r-1-carboxylic acid;

t-3-(1-Acetylamino-2-propyl)pentyl-c-4-amino-t-2-hydroxycyclopentane-r-1-carboxylic acid;

t-3-(1-Acetylamino-2-propyl)pentyl-c-4-(aminoimino)methylaminocyclopentane-r-1-carboxylic acid;

t-3-(1-Acetylamino-2-propyl)pentyl-c-4-aminocyclopentane-r-1-carboxylic acid;

Ethyl t-3-(1-Acetylamino-2-propyl)pentyl-c-4-(aminoimino)methylamino-t-2-hydroxycyclopentane-r-1-carboxylate;

Ethyl t-3-(1-Acetylamino-2-propyl)pentyl-c-4-amino-t-2-hydroxycyclopentane-r-1-carboxylate;

Ethyl t-3-(1-Acetylamino-2-propyl)pentyl-c-4-(aminoimino)methylaminocyclopentane-r-1-carboxylate;

Ethyl t-3-(1-Acetylamino-2-propyl)pentyl-c-4-aminocyclopentane-r-1-carboxylate;

t-3-(1-Acetylamino-3-ethyl)pentyl-c-4-(aminoimino)methylamino-t-2-hydroxycyclopentane-r-1-carboxylic acid;

t-3-(1-Acetylamino-3-ethyl)pentyl-c-4-amino-t-2-hydroxycyclopentane-r-1-carboxylic acid;

t-3-(1-Acetylamino-3-ethyl)pentyl-c-4-(aminoimino)methylaminocyclopentane-r-1-carboxylic acid;

t-3-(1-Acetylamino-3-ethyl)pentyl-c-4-aminocyclopentane-r-1-carboxylic acid;

Ethyl t-3-(1-Acetylamino-3-ethyl)pentyl-c-4-(aminoimino)methylamino-t-2-hydroxycyclopentane-r-1-carboxylate;

Ethyl t-3-(1-Acetylamino-3-ethyl)pentyl-c-4-amino-t-2-hydroxycyclopentane-r-1-carboxylate;

Ethyl t-3-(1-Acetylamino-3-ethyl)pentyl-c-4-(aminoimino)methylaminocyclopentane-r-1-carboxylate;

Ethyl t-3-(1-Acetylamino-3-ethyl)pentyl-c-4-aminocyclopentane-r-1-carboxylate.

The precursors according to the present invention are isoxazoline derivatives represented by the following formulae 4 and 10

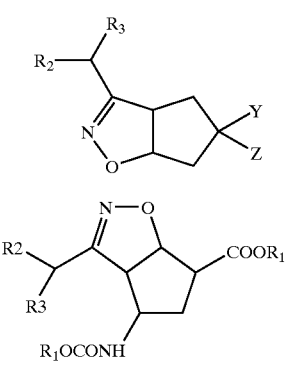

4

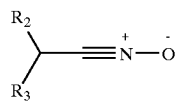

2 wherein $R_1$, $R_2$ and $R_3$ are the same as defined above and wherein each of Y and Z individually is $COOR_1$ or H provided that at least one of Y and Z is other than H.

The isoxazoline derivatives according to formula 4 are prepared according to scheme 1 illustrated below.

In particular, nitrile oxide of the formula 2 is reacted with a cyclopentane derivative of the formula 3 to produce the desired isoxazoline derivative. $R_2$, $R_3$ Y and Z are the same as defined above.

The nitrile oxides are conveniently prepared in situ by the method of Mukaiyama et al [J. Amer. Chem. Soc., Vol. 82, pp. 5339–5342 (1960)].

When Y is H, the derivatives obtained are cis/trans mixtures which optionally may be separated by conventional means such as chromatography or crystallization. When $Y=Z=COOR_1$, one of the carboxyl groups may be removed by selective hydrolysis and subsequent decarboxylation. Such selective hydrolysis may be achieved either chemically or enzymatically. After separation of the stereoisomers, the product may be further separated, by conventional means, into its two enantiomers in order to obtain an optically pure compound, if desired. Alternatively, by the suitable choice of chiral auxiliaries in Y or Z, the cycloaddition reaction may be achieved with enrichment of the desired enantiomer.

The cyclopentane compounds of formula 1a as illustrated in scheme 1 can be prepared from the above isoxazoline derivatives by reducing the isoxazoline derivatives of formula 4 to form an aminoalcohol derivative according to formula 5. The isoxazoline derivatives 4 can be reduced to form the aminoalcohol derivatives 5 directly by catalytic hydrogenation using catalysts such as Raney nickel or precious metal catalysts such as palladium or platinum. Alternatively, the reduction may be achieved with a chemical reducing agent such as a hydride reagent. If desired, by the choice of suitable reducing agents, such reductions may be done stereospecifically to obtain a single isomer. If a mixture of isomers is obtained, then separation of the isomers may be achieved by conventional separation techniques.

The aminoalcohol compound of formula 5 is reacted with an anhydride or acid halide, e.g. acid chloride, of a carboxylic acid of the formula: $R_1COOH$ to produce the acylated compounds represented by formula 6. Next the alcohol group of the acylated compounds is converted into a leaving group by conventional means. Examples of suitable leaving groups are tosylate and mesylate. The leaving group, in turn, is displaced by ammonia or guanidine to produce compounds of formula 1a. In the alternative, the leaving group can be displaced by an azide ion which in turn is converted to the guanidine using $NH_2$ compound.

In an alternative process for preparing the cyclopentane compounds of formula 1a, an isoxazoline compound of formula 4 is converted to ketone according to formula 7

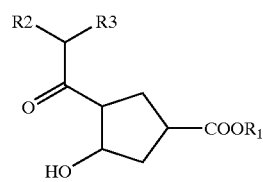

7 by opening its isoxazoline ring. The ring can be opened by hydrolysis.

The ketone of formula 7 is subjected to reductive amination to form a compound according to formula 8

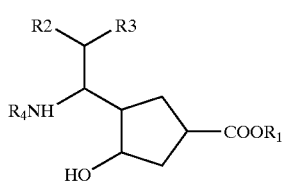

8 wherein $R_4$ is H or a benzyl group optionally substituted with an a-alkyl group of 1–3 carbon atoms.

If an optically pure benzyl derivative, e.g. (+)-or (−)-α-methylbenzyl is used, the reduction may be done stereospecifically. Further, the optical resolution may conveniently be performed at this stage.

When $R_4$ is a substituted benzyl, such is removed, for example by catalytic hydrogenation to give the aminoalcohol compounds of formula 5. The aminoalcohols are then converted to the final product as discussed above.

According to a still further aspect of the present invention, cyclopentane derivatives of formula 9 can be reacted with a nitrile oxide of formula 2 to give the isoxazoline derivatives 10 as shown in Scheme 2. Such isoxazolines may be converted to compounds 12 and may further be dehydrated to give the unsaturated compounds 13. Alternatively, the OH may be converted to $NH_2$ or F by conventional methods known in the art to afford compounds 14 and 15 respectively. Further, OH may be reacted with a carboxylic acid derivative $R_1COOH$, for example an acid anhydride to produce the esters —$OCOR_1$. Similarly, the $NH_2$ compound may be reacted with a carboxylic acid derivative to give $HNCOR_1$ or with an alkyl chloroformate derivative, $R_1OCOCl$, to give the carbamates $NHCOOR_1$.

Scheme 1
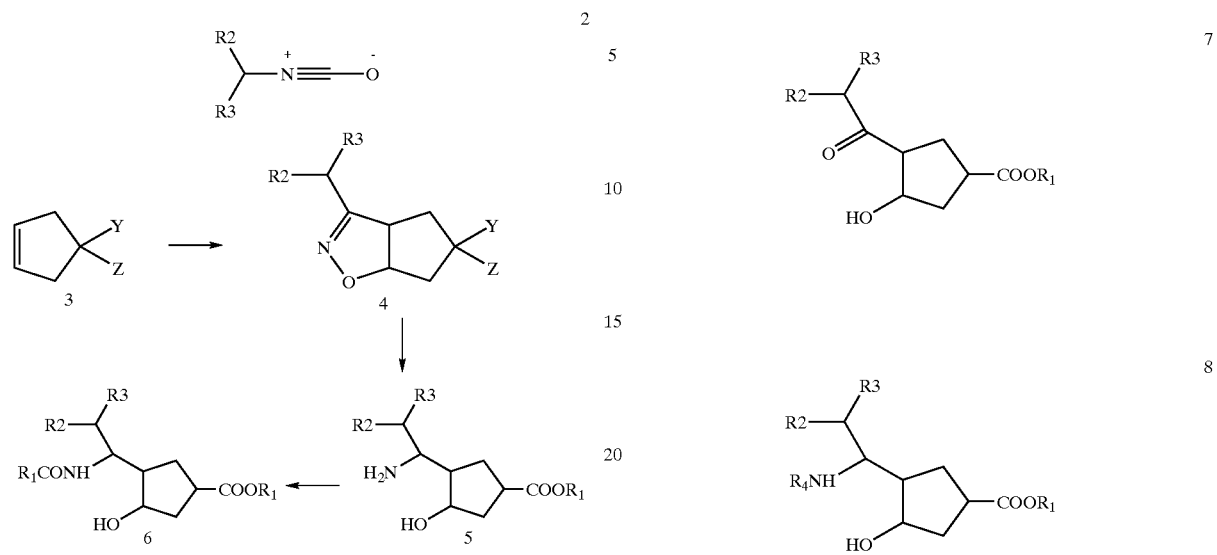
Scheme 2
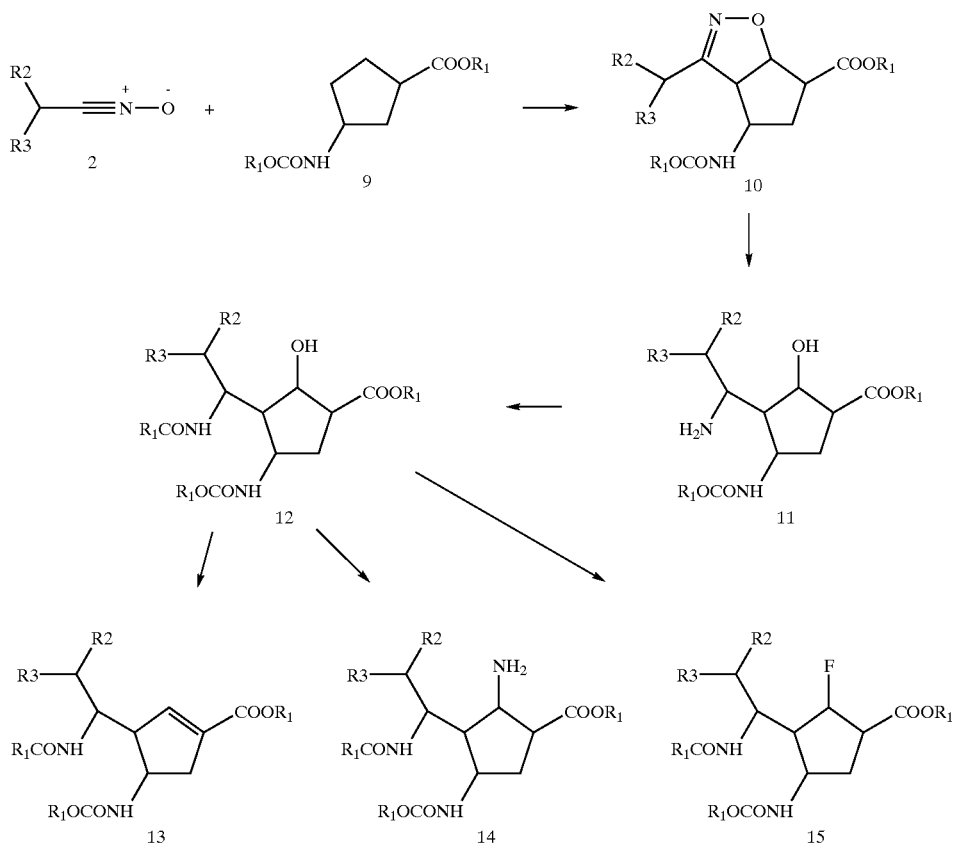

The following non-limiting examples are presented to further illustrate the present invention.

EXAMPLE 1

(−)-Ethyl cis-4-tert-butoxycarbonylamino-2-cyclopentene-1-carboxylate.

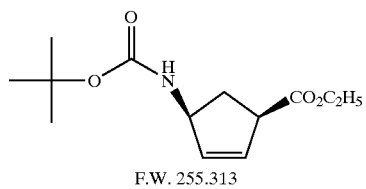

F.W. 255.313

A mixture of (−)-2-azabicyclo[2.2.1]hept-5-en-3-one (10 g, 91.7 mmol), ethanol (200 mL) and conc. HCl (10 mL) was heated at reflux for 2 h. The mixture was concentrated and the residue dried under vacuum. A white solid was obtained which was suspended in ether to give 17.5 g (100%) of (−)-ethyl cis-4-amino-2-cyclopentene-1-carboxylate hydrochloride.

To a mixture of (−)-ethyl cis-4-amino-2-cyclopentene-1-carboxylate hydrochloride (17.5 g, 91.3 mmol), in CH$_2$Cl$_2$ (200 mL) at 0° C., was added triethylamine (26 mL, 186.5 mmol), di-tert-butyldicarbonate (26 g, 119 mmol), and 4-dimethylaminopyridine (1 g, 8.2 mmol) and the mixture was stirred at room temperature for 16 h. The reaction mixture was washed with water (2×200 mL), and brine (50 mL), the organic layer was dried (MgSO$_4$) and concentrated in vacuo to furnish 21.3 g of crude product. Purification by flash column chromatography (silica gel 600 g, 20–50% ethyl acetate in hexane) gave 15.7 g (67%) of the product as a yellow oil.

EXAMPLE 2

Ethyl c-4-tert-butoxycarbonylamino-t-3-(2-propyl)butyl-4,5,6,6a-tetrahydro-3aH-cyclopent[d]isoxazole-6-r-carboxylate.

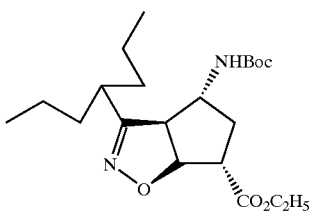

Phosphorus tribromide (33.3 g, 0.123 mol) was added dropwise to 2-propyl-1-pentanol (40 g, 0.307 mol) at −10° C. to maintain the temperature below 0° C. and the mixture was stirred overnight at room temperature. The reaction mixture was heated at 100° C. for 1 h, cooled to room temperature, and poured into ice water (250 ml). The organic layer was separated, washed with conc. H$_2$SO$_4$ (25 ml) followed by saturated K$_2$CO$_3$ (25 ml), dried and distilled in vacuo (80° C./15 mm Hg) to furnish 40 g (83%) of 1-bromo-2-propylpentane.

To a solution of sodium nitrite (30.6 g, 0.43 mol) in DMSO (700 ml) was added 1-bromo-2-propylpentane (49 g, 0.254 mol). The mixture was stirred overnight at room temperature and poured into ice water (700 g). The mixture was extracted with ether (4×250 ml), the organic layers were combined, washed with water (2×500 ml), brine (500 ml), dried and concentrated in vacuo to furnish 37.4 g (93%) of 1-nitro-2-propylpentane which was 85% pure based on $^1$H NMR data.

A mixture of 1-nitro-2-propylpentane (16 g, 75.4 mmol) and Et$_3$N (1.0 mL, 7.2 mmol) in benzene (75 ml) was added dropwise to a refluxing solution of (−)-ethyl-4-tert-butoxycarbonylaminocyclopentene-1-carboxylate (16.1 g, 62.9 mmol) and phenyl isocyanate (14.65 mL, 132.1 mmol) in benzene (125 ml) over 1 h. The mixture was boiled under reflux for 16 h, the solids were filtered off and washed with Et$_2$O (20 mL). The combined filtrates were concentrated to yield an orange oil. This crude product was purified by flash chromatography (750 g, SiO$_2$) using ethyl acetate (5%–20%) in hexane to give 15.75 g (62%) of ethyl c-4-tert-butoxycarbonylamino-t-3-(2-propyl)butyl-4,5,6,6a-tetrahydro-2aH-cyclopent[d]isoxazole-6-r-carboxylate.

EXAMPLE 3

(−)-Ethyl t-3-(1-acetylamino-2-propyl)pentyl-c-4-tert-butoxycarbonylamino-t-2-hydroxycyclopentane-r-1-carboxylate

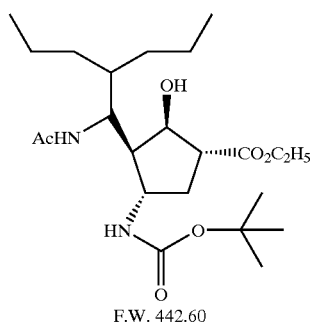

F.W. 442.60

To a mixture of ethyl c-4-tert-butoxycarbonylamino-t-3-(2-propyl)4,5,6,6a-tetrahydro-2aH-cyclopent[d]isoxazole-6-r-carboxylate (15 g, 39.8 mmol) in ethanol/water/acetic acid (1:1:1, 120 mL), was added PtO$_2$ (1.5 g). The reaction mixture was hydrogenated at 45 psi for 60 h. The catalyst was removed by filtration and the filtrate was concentrated to give 19 g of (−)-ethyl t-3-(1-amino-2-propyl)-pentyl-c-4-tert-botoxycarbonylamino-t-2-hydroxycyclopentane-r-1-carboxylate as an oil, which was used without further purification.

To a solution of the above compound (15.9 g, 39.8 mmol) in CH$_2$Cl$_2$ (200 mL) was added Ac$_2$O (8 mL, 80 mmol). The reaction mixture was stirred at room temperature for 2 h and poured into ice water (50 mL). The reaction mixture was neutralized with conc. NH$_4$OH. The organic layer was separated, washed with brine (50 mL), dried (MgSO$_4$) and concentrated in vacuo to furnish 17.6 g of crude product as an oil. Purification by flash column chromatography (silica gel 510 g, 50%, 75% and 100% EtOAc in hexane) gave 10.59 g (61%) of the product. Ether/hexane (10/50 mL) was added to the oil and stored in the freezer overnight. The crystals obtained were collected by filtration to furnish 4.0 g of the product as a white solid; mp 128–129° C.

EXAMPLE 4

(−)-Ethyl t-3-(1-acetylamino-2-propyl)pentyl-c-4-[(tert-butoxycarbonylamino-tert-butoxycarbonylimino)methyl]amino-t-2-hydroxycyclopentane-r-1-carboxylate

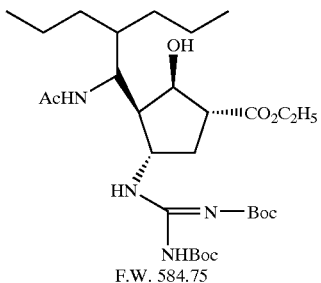

F.W. 584.75

To a solution of (−)-ethyl t-3-(1-acetylamino-2-propyl)pentyl-c-4-tert-butoxycarbonylamino-t-2-hydroxycyclopentane-r-1-carboxylate (0.5 g, 1.13 mmol) in $CH_2Cl_2$ (10 mL) was added trifluoroacetic acid (1.75 mL, 22.6 mmol). After stirring at room temperature for 16 h, the reaction mixture was concentrated and dried in vacuo to furnish (−)-ethyl t-3-(1-acetylamino-2-propyl)pentyl-c-4-amino-t-2-hydroxycyclopentane-r-1-carboxylate.

To the above compound dissolved in dry DMF (10 ml) was added $Et_3N$ (0.55 ml, 3.96 mmol), 1,3-bis(tert-butoxycarbonyl)-2-methyl-2-thiopseudourea (0.37 g, 1.24 mmol) and $HgCl_2$ (0.34 g, 1.24 mmol). The reaction mixture was stirred for 16 h at room temperature and was diluted with EtOAc (50 ml). The reaction mixture was filtered through Celite and washed with water (2×10 ml), brine (10 ml), dried ($MgSO_4$) and concentrated in vacuo to furnish 0.7 g of the crude product. The crude was purified by flash column chromatography (silica gel, 33 g, 20–30% EtOAc in hexane) to furnish 0.54 g (82%) of the product as a white foam, mp 42–43° C.

EXAMPLE 5

(−)-Ethyl t-3-(1-acetylamino-2-propyl)pentyl-c-4-[(aminoimino)methyl]amino-t-2-hydroxycyclopentane-r-1-carboxylate

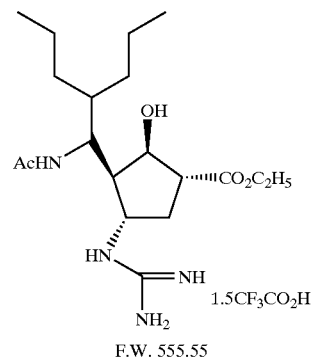

F.W. 555.55

A mixture of (−)-ethyl t-3-(1-acetylamino-2-propyl)pentyl-c-4-[(tert-butoxycarbonylamino-tert-butoxycarbonylimino)methyl]amino-t-2-hydroxycyclopentane-r-1-carboxylate (0.5 g, 0.85 mmol) in dichloromethane (10 mL) was stirred with trifluoroacetic acid (1.3 mL, 17.2 mmol) for 16 h at room temperature. The mixture was concentrated and co-evaporated with toluene (2×). The residue was triturated with ether-hexane to give 0.4 g (95%) of the product as a white solid, mp 105–107° C.

EXAMPLE 6

(−)-t-3-(1-Acetylamino-2-propyl)pentyl-c-4[(aminoimino)methyl]amino-t-2-hydroxycyclopentane-r-1-carboxylic acid

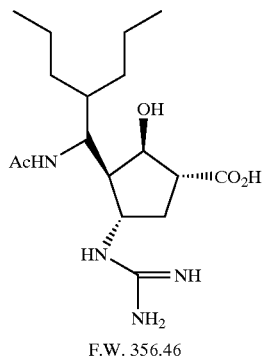

F.W. 356.46

A mixture of (−)-ethyl t-3-(1-acetylamino-2-propyl)pentyl-c-4-[(aminoimino)methyl]amino-t-2-hydroxycyclopentane-r-1-carboxylate (10.1 mg, 18 μmol), 1N sodium hydroxide (0.1 mL) and water (0.2 mL) was stirred at room temperature for 2 h, and neutralized with 1N HCl. The volume was adjusted to 1.0 mL with water to give 18.0 mmolar solution of the product.

EXAMPLE 7

(−)-Ethyl t-3-(1-acetylamino-2-propyl)pentyl-c-4-tert-botoxycarbonylamino-t-2-(1-imidazolythiocarbonyl)oxycyclopentane-r-1-carboxylate

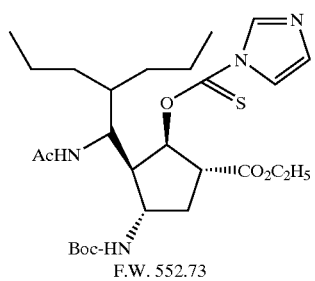

F.W. 552.73

To a mixture of (−)-ethyl t-3-(1-acetylamino-2-propyl)pentyl-c-4-tert-butoxycarbonylamino-t-2-hydroxycyclopentane-r-1-carboxylate (3.43 g, 7.76 mmol) in $CH_2Cl_2$ (50 mL) was added thiocarbonyldiimidazole (3.45 g, 19.41 mmol) and the mixture was heated under reflux for 16 h. The reaction mixture was cooled, washed with 0.25 N HCl (2.50 mL), water (50 mL) and brine (50 mL). The organic layer was dried ($MgSo_4$) and concentrated in vacuo to furnish 4.9 g of crude product. Purification by flash column chromatography (silica gel 295 g, 40–90% EtOAc in hexane) gave 1.23 g (29%) of the product as a white foam, mp 58–60° C.

EXAMPLE 8

(−)-Ethyl t-3-(1-acetylamino-2-propyl)pentyl-c-4-tert-butoxycarbonylaminocyclo-pentane-r-1-carboxylate

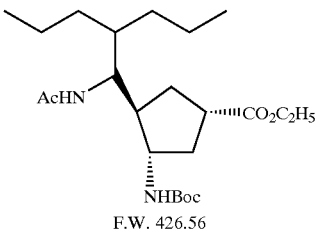

F.W. 426.56

To a solution of (−)-ethyl t-3-(1-acetylamino-2-propyl)pentyl-c-4-tert-butoxycarbonylamino-t-2-(1-imidazolylthiocarbonyl)oxycyclopentane-r-1-carboxylate (1.2 g, 2.17 mmol) in toluene (20 mL) at 70° C. was added AIBN (0.39 g, 2.39 mmol) followed by tributyltin hydride (0.64 mL, 2.39 mmol). The reaction mixture was heated at reflux for 5 minutes and concentrated in vacuo. The residue obtained was dissolved in EtOAc (20 mL) and was washed with 0.25 N HCl (2×20 mL), water (20 mL) and brine (20 mL). The organic layer was dried and concentrated in vacuo to furnish crude product as an oil. Purification by flash column chromatography (silica gel 46 g, hexane (2 L) to remove excess tributyltin hydride and 40–50% EtOAc in hexane) gave 0.84 g (91%) of the product as a white foam, mp 81–83° C.

EXAMPLE 9

(−)-Ethyl t-3-(1-acetylamino-2-propyl)pentyl-c-4-[(tert-butoxycarbonylamino-tert-butoxycarbonylimino)methyl]aminocyclopentane-r-1-carboxylate hydrate[4:1]

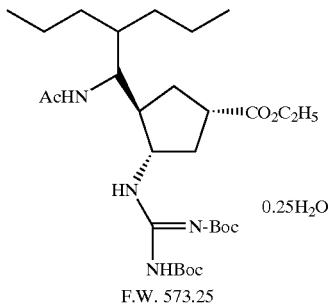

F.W. 573.25

To a solution of (−)-ethyl t-3-(1-acetylamino-2-propyl)pentyl-c-4-tert-butoxycarbonylaminocyclopentane-r-1-carboxylate (0.84 g, 1.97 mmol) in CH$_2$Cl$_2$ (20 mL) was added trifluoroacetic acid (2.28 mL, 29.6 mmol) and stirred at room temperature for 16 h. The reaction mixture was concentrated and dried in vacuo to furnish (−)-ethyl t-3-(1-acetylamino-2-propyl)pentyl-c-4-aminocyclopentane-r-1-carboxylate.

To the above compound dissolved in dry DMF (20 ml) was added Et$_3$N (0.97 ml, 6.9 mmol), 1,3-bis(tert-butoxycarbonyl)-2-methyl-2-thiopseudourea (0.64 g, 2.17 mmol) and HgCl$_2$ (0.59 g, 2.17 mmol). The reaction mixture was stirred for 16 h at room temperature and was diluted with EtOAc (50 ml). The reaction mixture was filtered through Celite and the filtrate was washed with water (2×10 ml), brine (10 ml), dried (MgSO$_4$) and concentrated in vacuo to furnish 1.27 g of the crude product. The crude was purified by flash column chromatography (silica gel 56 g, 30–40% EtOAc in hexane) to furnish 0.82 g (73%) of the product as a white foam, mp 42–43° C.

EXAMPLE 10

(−)-Ethyl t-3-(1-acetylamino-2-propyl)pentyl-c-4-[(aminoimino)methyl]aminocyclopentane-r-1-carboxylate

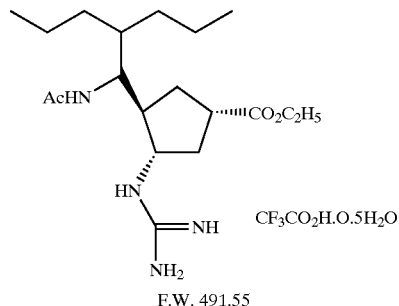

F.W. 491.55

To a solution of (−)-ethyl t-3-(1-acetylamino-2-propyl)pentyl-c-4-[(tert-butoxycarbonylamino-tertbutoxycarbonylimino)methyl]aminocyclopentane-r-1-carboxylate (0.8 g, 1.4 mmol) in CH$_2$Cl$_2$ (15 mL) was added (2.2 mL, 28.2 mmol) of trifluoroacetic acid and stirred at room temperature for 16 h. The reaction mixture was concentrated and co-distilled with toluene (2×) in vacuo to furnish product as a white residue. The residue was triturated with ether/hexane to furnish 0.5 g (72%) of the product as a white solid, mp 56–58° C.

EXAMPLE 11

(−)-t-3-(1-Acetylamino-2-propyl)pentyl-c-4-[(amino-imino)methyl]aminocyclopentane-r-1-carboxylic acid

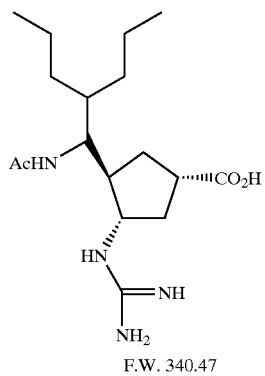

F.W. 340.47

A mixture of (−)-ethyl t-3-(1-acetylamino-2-propyl)pentyl-c-4-[(amino-imino)-methyl]aminocyclopentane-r-1-carboxylate (10.2 mg, 21 μmol), 1N sodium hydroxide (0.1 mL) and water (0.2 mL) was stirred at room temperature for 2 h and neutralized with 1N HCl. The volume was then adjusted to 1.0 mL with water to give a 14.9 mmolar solution of the product.

Dosage and Formulation

The antiviral compounds prepared by the processes of this invention can be administered as treatment for viral infections by any means that produces contact of the active agent's site of action with the viral neuraminidase in the body of a human, mammal, bird, or other animal. They can be administered by an conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desired. A daily dosage of active ingredient can be expected to be about 0.001 to 1000 milligram (mg) per kilogram (kg) of body weight, with the preferred dose being 0.1 to about 30 mg/kg.

Dosage forms (compositions suitable for administration) contain from about 1 mg to about 100 mg of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. The active ingredient can also be administered intranasally (nose drops) or by inhalation.

Other dosage forms are potentially possible such as administration transdermally, via a patch mechanism or ointment.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propylparaben, and chlorobutanol.

Suitable pharmaceutical carriers are described in Remington's Pharmaceutical Sciences, Mack Publishing Company, a standard reference text in this field.

Useful pharmaceutical dosage forms for administration of the compounds prepared according to the present invention can be illustrated as follows:

Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into gelatin to form soft gelatin capsules containing 100 mu of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate coatings may be applied to increase palatability or delay absorption.

Moreover, the compounds of the present invention can be administered in the form of nose drops or a nasal inhaler.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

What is claimed is:

1. A method for preparing a substituted cyclopentane compound represented by formulae 1a or 1b

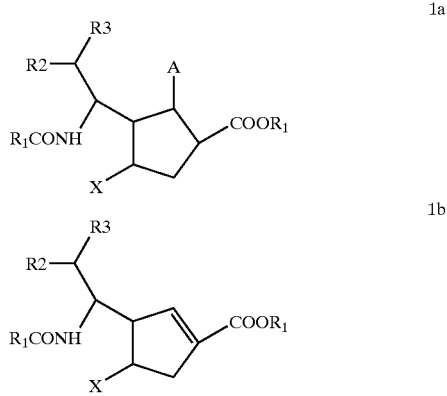

wherein each $R_1$ individually is alkyl or substituted alkyl, alkenyl or substituted alkenyl of 1–6 carbon atoms, or H; each of $R_2$ and $R_3$ individually is alkyl or alkenyl of 1–8 carbon atoms, cycloalkyl or substituted cycloalkyl of 4–8 carbon atoms, aryl or substituted aryl, arylalkyl or substituted arylalkyl, or H provided at least one of $R_2$ and $R_3$ is other than H; X is $NHR_1$, $NHC(=NH)NHR_4$ where $R_4$ is H, alkyl of 1–6 carbon atoms, $OR_1$, $COR_1$, $COOR_1$, CN, or $NO_2$; A is H, F, $OR_1$, $OCOR_1$, —$OOCNHR_1$, $NHR_1$, or $NHCOOR_1$; and pharmaceutically acceptable salts thereof;
which comprises:
Step (1) obtaining an isoxazoline compound of formula 10;

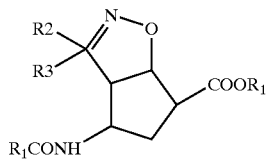

wherein each $R_1$ individually is alkyl or substituted alkyl, alkenyl or substituted alkenyl of 1–6 carbon atoms; or H; each of $R_2$ and $R_3$ individually is alkyl or alkenyl of 1–8 carbon atoms; cycloalkyl or substituted cycloalkyl or 4–8 carbon atoms, aryl or substituted aryl, arylalkyl or substituted arylalkyl, or H provided at least one of $R_2$ and $R_3$ is other than H;

which comprises reacting a nitrite oxide of formula 2

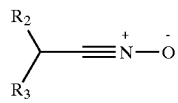

with a cyclopentane derivative having formula 9

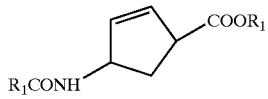

to produce said isoxazoline compound;

Step (2) converting said isoxazoline to a compound of formula 12

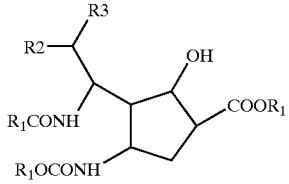

and dehydrating said compound of formula 12 to produce a compound of formula 13

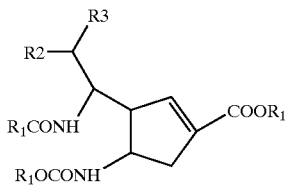

or converting the OH groups of said compound of formula 12 to a group selected from F, $OR_1$, $OCOR_1$, $NHR_1$ or $NHCOOR_1$, except when said group is $OR_1$, $R_1$ is other than H.

* * * * *